US00PP18810P2

(12) United States Plant Patent
Oud et al.

(10) Patent No.: US PP18,810 P2
(45) Date of Patent: May 13, 2008

(54) *LOBELIA* PLANT NAMED 'LOBTRABLU'

(50) Latin Name: *Lobelia erinus*
Varietal Denomination: Lobtrablu

(75) Inventors: Johannes Simon Nicolaas Oud, Bovenkarspel (NL); Theodorus Cornelia Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/648,946

(22) Filed: Jan. 3, 2007

(51) Int. Cl.
*A01H 5/00* (2006.01)

(52) U.S. Cl. ..... Plt./451

(58) Field of Classification Search ..... Plt./451, Plt./263
See application file for complete search history.

*Primary Examiner*—Wendy C. Haas
(74) *Attorney, Agent, or Firm*—S. Matthew Edwards

(57) ABSTRACT

A new *Lobelia* plant particularly distinguished by its spreading plant habit, strong branching, large flower size, and deep blue flower color.

1 Drawing Sheet

Latin name of the genus and species of the plant claimed: *Lobelia erinus.*
Varietal denomination: 'Lobtrablu'.

BACKGROUND OF THE NEW PLANT

The present invention relates to a new and distinct cultivar of *Lobelia* plant. The new cultivar is propagated by cuttings resulting from the cross between *Lobelia erinus* 'Z0892-1' and *Lobelia erinus* 'A0951-1.' 'A0951-1' is a blue flower color selection of our own breeding, having a spreading habit, very strong growth, good branching plant habit, and being early flowering. 'Z0892-1' is a blue flower color selection of our own breeding, having a medium growth, trailing plant habit, and being late flowering. Neither 'A0951-1' nor 'Z0892-1' has been patented.

As a result of this cross the present cultivar was created in 2001 in Enkhuizen, Netherlands and has been repeatedly asexually reproduced by cuttings in Enkhuizen over a five year period. It has retained its distinctive characteristics through successive propagations and is firmly fixed.

DESCRIPTION OF THE PHOTOGRAPH

This new *Lobelia* plant is illustrated by the accompanying photograph which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Lobelia.* The data, which defines these characteristics, were collected from asexual reproductions carried out in Enkhuizen, Netherlands. The plant history was taken on 30 week old plants.

TABLE 1

DIFFERENCES BETWEEN 'LOBTRABLU' AND TWO SIMILAR CULTIVARS

| Characteristic | 'Lobtrablu' | 'Wesstar' (U.S. Plant Patent No. 12,678) | 'Ricardii' (Not patented) |
|---|---|---|---|
| plant | | | |
| Height | Up to 15 cm | 20 cm | 30 cm |
| Width | 50 cm | 50 cm | 60 cm |
| Shape | Spreading | Spreading | Spreading |
| flower color | | | |
| Upper surface | 94A | 96A with spots darker than 95A | 94A |
| Lower surface | 94B | 96C | 94B |
| Flower tube | 93A | 94A | 94B |

No descriptions of parent lines are available. The only info is mentioned as background of the new plant on page 1.

The plant:

*Classification.*—Botanical : *Lobelia erinus.*

*Parentage.*—Female parent : A seedling named 'Z0892-1' is one of our seedlings from our Z-generation of plants bred in 1998. Male parent : A seedling named 'A0951-1' is one of our seedlings from our A-generation of plants bred in 1999.

*Growth habit.*—Spreading to upright.

*Plant height.*—Up to 15 cm.

*Spreading area of plant.*—50 cm.

*Growth rate.*—Strong growth.

*Strength.*—Good, excellent.

*Branching character.*—Freely branching and lateral branching at every node. Pinching will enhance branching. Branches strong and flexible.

*Blooming period.*—From May until October.

The stem:

*Diameter.*—0.3 cm.

*Length.*—30 cm.

*Texture.*—Smooth, slightly glossy (young stem smooth, old stem smooth glossy).

*Color.*—RHS 137C in old stems, RHS 143B in young stems. Occassionally some anthocyan in old stem, RHS 166A.

*Length of internode.*—0.5–3.8 cm, depending on the light conditions where the plant is grown, and the age of the stem.

*Shape.*—(Tri)angular.

The foliage:

*Shape.*—Leaves simple, generally symmetrical and flat. Broadly ovate with rounded apex, attenuate base and dentate margin in leaves of juvenile plant; lanceolate to ensiform in leaves of mature plant with entire margin.

*Texture.*—Glossy on upper and lower side.

*Length.*—2.5 cm (leaves of juvenile plant up to 4 cm, leaves of mature plant up to 3 cm).

*Width.*—In leaves of juvenile plants 2 cm, leaves of mature plant 0.7 cm.

*Color.*—Upper surface : RHS 146A in old leaves, RHS 137C in young leaves. Lower surface : RHS 146B in old leaves, RHS 137D in young leaves Foliage color applies for juvenile as well as mature phase.

*Veins.*—Pinnate, upper side RHS 137D, lower side RHS 137D.

*Length of petiole.*—Not present.

The flower:

*Type and habit.*—Flower form at apical axils, usually one flower per axil. Flowers labiate, upper lip consisting of two small petals and lower lip consisting of three larger and broader petals. Petals have obovate shape with a mucronulate apex and entire margin.

*Lastingness on the plant.*—10–14 days depending on temperature. Petals are fused at base into a tube. Freely and continuously flowering, around 100–150 flowers. Flowers face outward.

*Width.*—Petal: Upper petals 0.2 cm, lower petals: for lower central petal 0.4 cm, for other lower petals 0.6 cm.

*Length.*—Petal: Upper petals 0.6 cm, lower petals 0.9 cm.

*Depth.*—Flower: 1.5 cm.

*Diameter.*—Flower: 1.5 cm.

*Texture.*—Smooth, very lightly pubescent, upper and lower side.

*Buds.*—Length: 1 cm. Diameter: 0.3 cm. Form: Tubular. Color: Top RHS 94A, more 94C towards base.

*Flower color.*—Upper surface: RHS 94A, vein in flower 93A. Lower surface: RHS 94B. Flower tube (outside): RHS 93A on upper side, 97D on lower side with spots of 94A. Remarks: On the three lower petals of flower, there is a white spot, width 0.5 cm, depth 0.5 cm, color white than RHS 155D. There is not a white spot on the upper petals. At the base of the lower petals, where the throat starts, there are two yellow marking into the throat (Length 0.1 cm, width 0.5 mm, RHS 2A).

*Throat.*—Texture: Whiskered. Depth: 0.6 cm. Diameter: 0.2 cm. Color: Whiter than RHS 155D with spots darker than RHS 94A.

*Sepals.*—No. of sepals: 5. Length: 0.8 cm. Width: 0.1 cm. Texture: Smooth. Color: RHS 146A upper side and RHS 146A lower side. Shape: Linear. Apex: Acute. Margin: Entire. Sepals are fused at base.

*Flower stem.*—Length: 1.8–2.2 cm. Angle: Begins upright in early flowering; more at the angle 45° to stem in older flower. Strength: Rigid, flexible. Color: RHS 143B. Diameter: 0.3 mm.

Reproductive Organs:

*Androecium.*—Stamen number: 5. Anther shape: Oblong. Anther length: 2 mm. Anther color: RHS 200B. Pollen color: RHS 4D. Amount of pollen: Abundant.

*Gynoecium.*—Pistil length: 0.7 cm. Stigma shape: Trilobed. Stigma diameter: 0.5 mm. Stigma color: RHS 95A with very bright tip of RHS 87B. Style color: RHS 92A near stigma, RHS N144C towards base. Ovary color: RHS 144C.

Seed development: Some seed development has been observed on plants of new *Lobelia.*

*Seed.*—Color : RHS N199B. Shape: Round. Size: Very small, 'like dust'. Amount per seed pod: Approximately 2000.

Fruit:

*Size.*—Diameter : 0.2 cm. Length: 0.5 cm.

*Color.*—RHS 143B.

Disease resistance: No susceptibility or resistance to fungal, bacterial or viral pathogens has been noted.

What is claimed is:

1. A new and distinct variety of *Lobelia* plant, named 'Lobtrablu,' as illustrated and described herein.

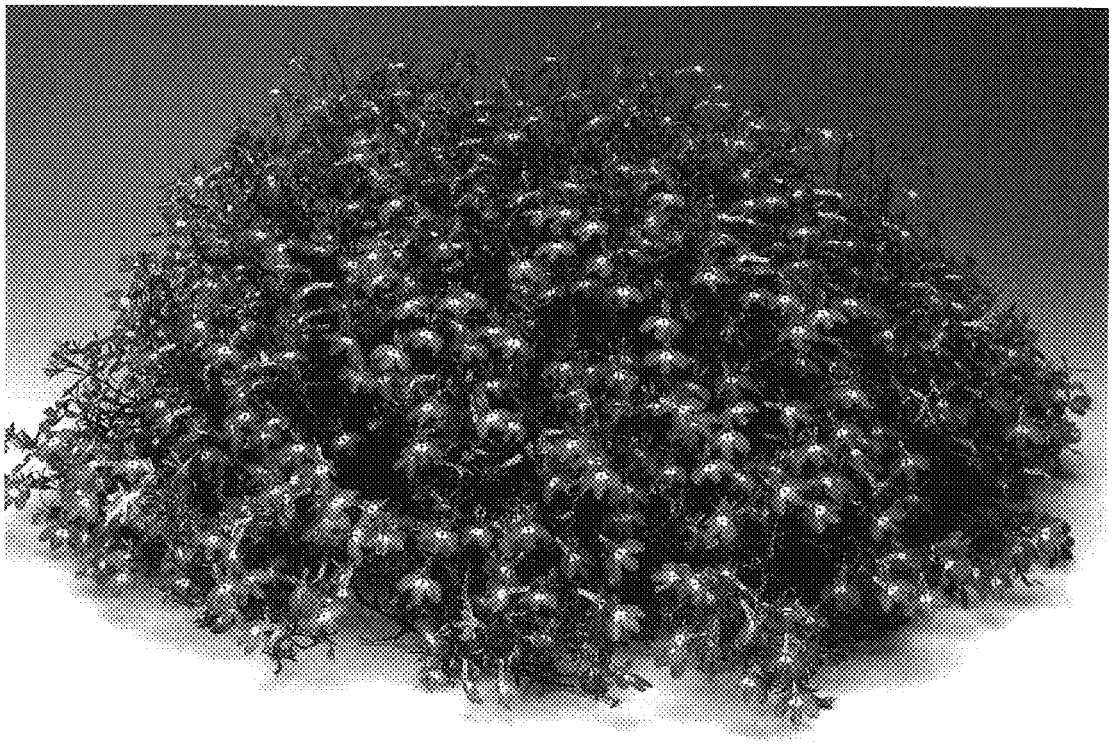

* * * * *